(12) United States Patent
Syed

(10) Patent No.: US 11,045,395 B2
(45) Date of Patent: Jun. 29, 2021

(54) SMART LID SLEEVE SYSTEMS TO FACILITATE MANAGEMENT OF NOTIFICATIONS AND ALERTS ASSOCIATED WITH CONTAINERS

(71) Applicant: Naim Ulhasan Syed, Canterbury, NH (US)

(72) Inventor: Naim Ulhasan Syed, Canterbury, NH (US)

( * ) Notice: Subject to any disclaimer, the term of this patent is extended or adjusted under 35 U.S.C. 154(b) by 0 days.

(21) Appl. No.: 16/684,225

(22) Filed: Nov. 14, 2019

(65) Prior Publication Data

US 2020/0146942 A1 May 14, 2020

Related U.S. Application Data

(60) Provisional application No. 62/767,324, filed on Nov. 14, 2018.

(51) Int. Cl.
*A61J 7/04* (2006.01)
*B65D 51/24* (2006.01)
*A61J 1/03* (2006.01)
*B65D 41/62* (2006.01)

(52) U.S. Cl.
CPC ............... *A61J 7/0436* (2015.05); *A61J 1/03* (2013.01); *B65D 41/62* (2013.01); *B65D 51/248* (2013.01)

(58) Field of Classification Search
CPC ........ B65D 43/02; B65D 41/62; B65D 43/00; B65D 43/0235; B65D 43/08; A61J 7/0436; A61J 1/03
USPC .................................................... 340/309.16
See application file for complete search history.

(56) References Cited

U.S. PATENT DOCUMENTS

| | | | |
|---|---|---|---|
| 2002/0093427 A1* | 7/2002 | Roth | G08B 21/24 340/573.1 |
| 2005/0151625 A1* | 7/2005 | Lai | G08B 21/24 340/309.16 |
| 2014/0266760 A1* | 9/2014 | Burke, Jr. | G06F 19/3462 340/687 |

* cited by examiner

*Primary Examiner* — Emily C Terrell

(57) ABSTRACT

Disclosed herein is a smart lid sleeve system in accordance with some embodiments. Further, the smart lid sleeve system may include a lid sleeve, at least one sensor, a processing device, a storage device, a transmitter, and a power source. Further, the lid sleeve may include a first part and a second part. Further, the at least one sensor disposed on the lid sleeve. Further, the processing device communicatively coupled with the at least one sensor. Further, the processing device may be configured for analyzing the at least one sensor data. Further, the processing device may be configured for generating at least one notification based on the analyzing. Further, the storage device configured for storing the at least one notification. Further, the transmitter communicatively coupled with the processing device. Further, the power source electrically coupled with the at least one sensor, the transmitter, the processing device, and the storage device.

18 Claims, 16 Drawing Sheets

SMART LID SLEEVE SYSTEMS TO FACILITATE MANAGEMENT OF NOTIFICATIONS AND ALERTS ASSOCIATED WITH CONTAINERS

FIELD OF THE INVENTION

Generally, the present disclosure relates to the field of data processing. More specifically, the present disclosure relates to smart lid sleeve systems to facilitate the management of notification associated with containers.

BACKGROUND

Many people have become accustomed to a routine as they get up in the morning and take an assortment of medications for the day. These medications may be placed in specially designed plastic containers that allow the organizing of the medications by each day of the week. While this system may be simple and work for many elderly and adults, but some consistently forget to take their medications or if they've taken them already for the designated day. These delays can have harmful effects on the person and can lead to complications.

Existing techniques for taking medications are deficient with regard to several aspects. For instance, current technologies do not notify about scheduled medications. Furthermore, current technologies do not keep track of the medications. Moreover, current technologies allow misuse/overdose of medicines.

Therefore, there is a need for an improved smart lid sleeve systems to facilitate the management of notification associated with containers that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a smart lid sleeve system in accordance with some embodiments. Further, the smart lid sleeve system may include a lid sleeve, at least one sensor, a processing device, a storage device, a transmitter, and a power source. Further, the lid sleeve may include a first part and a second part. Further, the first part may be configured to attach to a lid of a container. Further, the second part may be configured to attach to a neck of the container proximal to a container opening of the container. Further, the lid may be configured to be openably coupled with the container opening. Further, the lid may be associated with a plurality of coupling states in relation to the container opening. Further, the at least one sensor disposed on the lid sleeve. Further, the at least one sensor may be configured for generating at least one sensor data. Further, the at least one sensor data corresponds to the plurality of coupling states. Further, the processing device communicatively coupled with the at least one sensor. Further, the processing device may be further configured for analyzing the at least one sensor data. Further, the processing device may be configured for generating at least one notification based on the analyzing. Further, the at least one notification may include a coupling indicator associated with the lid. Further, the storage device configured for storing the at least one notification. Further, the transmitter communicatively coupled with the processing device. Further, the transmitter may be configured for transmitting the at least one notification to at least one user device associated with at least one user. Further, the power source electrically coupled with the at least one sensor, the transmitter, the processing device, and the storage device. Further, the power source may be disposed on the lid sleeve.

Further disclosed herein is a smart lid sleeve system, in accordance with some embodiments. Accordingly, the smart lid sleeve system may include a container, a lid, a lid sleeve, at least one sensor, a processing device, a storage device, a transmitter, and a power source, a container configured to store at least one object. Further, the container may include a container opening and a container neck. Further, the container opening may be shaped in at least one opening shape. Further, the lid may be configured to be openably coupled with the container opening. Further, the lid may be associated with a plurality of coupling states in relation to the container opening. Further, the lid sleeve may include a first part and a second part. Further, the first part may be configured to attach to the lid. Further, the second part may be configured to attach to the neck of the container proximal to the container opening. Further, the at least one sensor disposed on the lid sleeve. Further, the at least one sensor may be configured for generating at least one sensor data. Further, the at least one sensor data corresponds to the plurality of coupling states. Further, the processing device communicatively coupled with the at least one sensor. Further, the processing device may be further configured for analyzing the at least one sensor data. Further, the processing device may be configured for generating at least one notification based on the analyzing. Further, the at least one notification may include a coupling indicator associated with the lid. Further, the storage device configured for storing the at least one notification. Further, the transmitter communicatively coupled with the processing device. Further, the transmitter may be configured for transmitting the at least one notification to at least one user device associated with at least one user. Further, the power source electrically coupled with the at least one sensor, the transmitter, the processing device, and the storage device. Further, the power source may be disposed on the lid sleeve.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION

Figure 1:
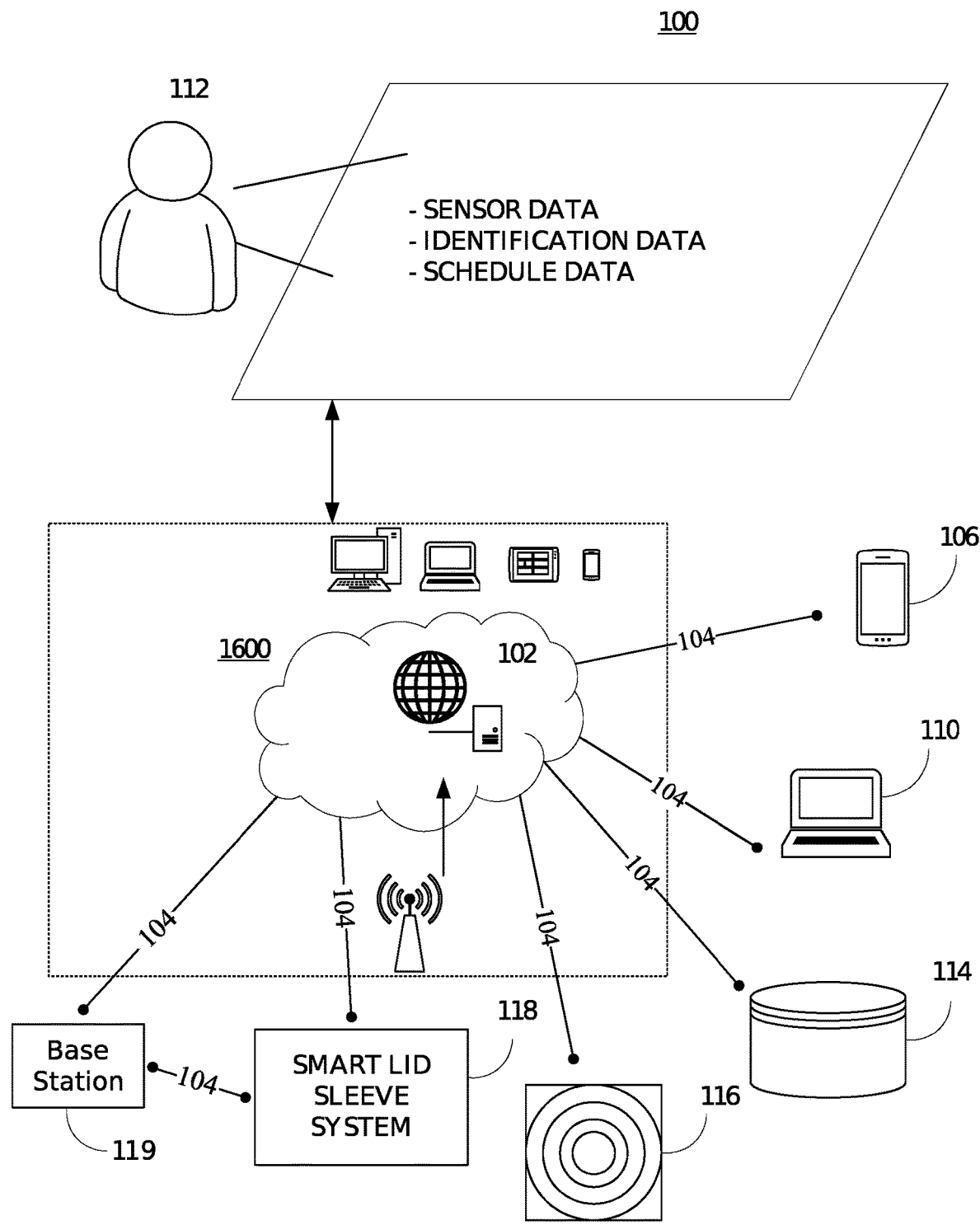
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of smart lid sleeve systems to facilitate the management of notification associated with containers, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor, and at least one actuator. Examples of the one or more client devices and/or the server computer may include, a desktop computer, a laptop computer, a tablet computer, a personal digital assistant, a portable electronic device, a wearable computer, a smartphone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice-based interface, gesture-based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third-party database, a public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of the transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role-based access control, and so on.

Further, one or more steps of the method disclosed herein may be initiated, maintained, controlled and/or terminated based on a control input received from one or more devices operated by one or more users such as, for example, but not limited to, an end-user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human-readable secret data (e.g. username, password, passphrase, PIN, secret question, secret answer etc.) and/or possession of a machine-readable secret data (e.g. encryption key, decryption key, bar codes, etc.) and/or or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smartcard with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human-readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between the performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview:

The present disclosure describes smart lid sleeve systems to facilitate the management of notification associated with containers. The present disclosure relates generally to an apparatus and/or systems to facilitate the management of notification associated with containers. Further, the management of notification may include alerts and reminders for a scheduled task associated with the containers. Further, the management of notification may include generating a notification of pilferage, compliance, and alert of any unwanted activity associated with the containers. Further, the particular use-case scenarios for the notification may include a medication reminder for compliance and alert in case of the unwanted activity or as an alert for a liquor bottle (containers) being opened. Further, the present disclosure may be used as an apparatus and/or systems for a medication reminder system that will assist a patient in reminding, tracking, recording, and communicating with the allowed recipients drug regimen. Alternatively, it can be an alert system if the medicine bottle is opened by someone who is not desired to open it to misuse it.

The present disclosure looks to introduce an apparatus for a medication reminder system that will assist the patient in reminding, tracking, recording, and communicating with the allowed recipient's drug regimen. In another scenario, fueled by accessibility and high demand, medication theft—coined "pharmaceutical diversion" by the U.S. Drug Enforcement Administration—has escalated in recent years. The National Drug Intelligence Centre. reported that S184 million in prescription drug thefts occurred in 2010—a 350 percent increase since 2007, these numbers are escalating since, in 2016, an estimated 6.2 million Americans aged 12 or older misused psychotherapeutic drugs at least once in the past month, which represents 2.3 percent of the population aged 12 or older. Particularly vulnerable are older adults, who may fall victim to unscrupulous caregivers or family members, or even to strangers hunting for an easy target. The present disclosure will help control this crisis and the application will alert the patient or the care giver in real-time.

Scope:

The present disclosure is a reminder, alert and notification system built for a dispenser. The setup will assist the user in reminding, tracking, recording, and communicating with the allowed recipient. In an example, a reminder comprises of a chip attached to the lid of a dispenser programmable to do the following:

Send out a signal to the database once the cap is opened. A sensor detects this action and registers that the action has been taken and registers it in the system for the first time. This information is then sent to the base station connected wirelessly, it is stored in the database and based on its utility this information is sent online to update a mobile application, where it can get manipulated to provide various pre-determined functions benefiting the user and its caregivers. For example, if the alert is used for medication reminder, it will utilize the information to register the time the medicine was taken and compare it with the information stored in the app and qualify the usage. In case of a delayed alert, the app can remind the user of delay. Connecting and relaying the information to a smartphone or a smart device will help secure a user to be able to the timely dispensation of the medicine or the illicit operation without consent to control pharmaceutical diversions.

Steps:
 1. A device that connects using Bluetooth to a base station. This base station holds the information in real-time and transmits using internet or mobile connectivity to an online database, this database is the source of information for the mobile app that gets updated instantly.
 2. In case the base device is interrupted and not connected to the internet or the mobile device, it saves the alerts until the time it connects back and transfers the information.
 3. Mobile application (Android and iOS) is able to schedule alerts and reminders. It also includes the functions provided in the project scope above.

Concept & Components:

The project is a smart lid for bottle containers such as medicine bottles, expensive liquids (liquor bottles, etc.) where the opening and closing are recorded and the user is notified in case the missed a scheduled action i.e. taking a pill or unwanted use of the bottle. The mobile app associated with the notification adds further functionalities such as alarm, notification, and alerts. By accessing the stored data in the cloud. The focus of this document is to define the operation of the "smart Lid" and the "base station".

Smart Lid:

The Smart lid consists of a small coin cell powered module fitted over the original medicine bottle cap. It is paired with an elastic ring that stores one or more magnets or some other form of magnetic material. The purpose of the lid is to work-out if it is removed from the bottle and to record/send the data to the base station. Cost and size are the two major factors in the design.
 1. Details:
    a. The sensor will sense the magnet. A range of 0 mm to 10 mm and as the connect breaks it to send a signal.
    b. The Sensor will distinguish between its own magnet and magnets on bottles adjacent to itself.
    c. Connection range. The chip/module is ultra-low powered to extend the battery life.
 2. Details and Concepts: The smart lid is to use a simple Hall Effect or magneto resistive sensor. Low power devices which can deliver either a digital level or analogue output. Connectivity is via a small proprietary format 2.43 GHz connection. Using a single access sensor will require the least amount of processing, a simple level, and threshold is required.
 3. Lid Hardware Design: The lid is designed to fit in a 27 mm or comparable size of the bottle disk. Battery location offset to allow for unobstructed RF mounted on the top side, electronics on the bottom side. The processor of choice that can work effectively. A processor for its ultra-low power operation will be preferred. It is preferred that the process has a 10-bit ADC, a comparator, a CRC generator, a Timer (Type B), a UART/SPI (but not I2C) and a RTC (counter).
 4. Lid Firmware Design: The primary focus of the design is low power. Each Lid will have an individual serial number, programmed at the manufacturer for a 32-bit unique ID. The sensor is read at set intervals (250-500 ms) and if the result shows the magnetic field crosses a pre-set threshold, the transceiver is started and a packet is sent. The packet includes a unique ID, timestamp showing the difference between sample time and the present time and the new value (on/off) The packet is retried at various intervals until successful or it gives up after 10 retires. Retries will automatically update the send time. The FRAM of the processors main storage is similar to RAM in operation, it can be written with the last value, count, etc. and will survive power cycling. If there is a communication failure occurs, the value will be saved and will attempt to transmit again and again until it is transmitted. An omnidirectional sensor which changes resistance when exposed to a magnetic field is used. This is pivoted on the bottle side of the device and the Chip/module is on the lid side. Once the lid is removed from the bottle the connection breaks and signals are sent out. The MSP430's ADC or a comparable unit will be used in proportional mode, it will read the voltage division rather than absolute value (since the supply rail will start at 3 V and drop to 2 V). This avoids having to calculate what the supply rail is so as to determine the correct resistor divider voltage. The ADC and should be-able to distinguish 3 mV steps in this mode (referenced to the 3V), however accuracy doesn't increase at lower voltages as the result is ratio metric. Using oversampling techniques and oversampling the ADC 16 times, 0.7 mV steps will be achievable (two extra bits allowing easy detection at these small values.

Base Station:

The base station is mainly powered with the ability to display information to the user. It must be simple to operate with graphical menus; Internationalization of languages are also important. It must be able to access current time and also recover the time when powered off (and no Wi-Fi network is within range). It must be able to access the Internet; Wi-Fi is the chosen method. For keyboard access, it would be good to access BLE so it can directly talk with a smartphone. This can also be used as an alternate Internet Access (via cellular connectivity). The base station uses a powerful processor with more capabilities because of security, connectivity, and information disbursement.

1. Base Station Hardware Design: A 2.5" comes with a display of 70.4×45.8 mm or comparable with a visible area of 57×38 mm, these numbers can be adjusted to make the unit more usable. The processor of choice will be used for a secure processing with encryption and low power features on board. For storage, the flash will be added. It also has an internal battery-backed real-time clock.
2. Base Station Firmware Design: The operational focus is on maintaining the correct time and communicating with the Smart Lids. The remaining tasks are user interaction this includes setting the time, informative messages, alerts, etc. and Cloud updates. It should also be possible to send alerts to a predefined user over the BLE connection (if it is within range).

Initial Tasks: The signals sent from the smart lids will be intercepted by the BASE and will hold the information and will transmit it to the cloud server. Multiple days of information will be saved on the device so that the information is accessible in case of transmission failure or in case of local needs to keep the information.

Referring now to figures, FIG. 1 is an illustration of an online platform 100 consistent with various embodiments of the present disclosure. By way of non-limiting example, the online platform 100 to facilitate the management of notification associated with containers may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114, sensors 116, a smart lid sleeve system 118, and a base station 119 over a communication network 104, such as, but not limited to, the Internet. Further, users of the online platform 100 may include relevant parties such as, but not limited to, end-users, administrators, service providers, service consumers and so on. Accordingly, in some instances, electronic devices operated by the one or more relevant parties may be in communication with the platform.

A user 112, such as the one or more relevant parties, may access online platform 100 through a web-based software application or browser. The web-based software application may be embodied as, for example, but not be limited to, a website, a web application, a desktop application, and a mobile application compatible with a computing device 1600.

Figure 2:
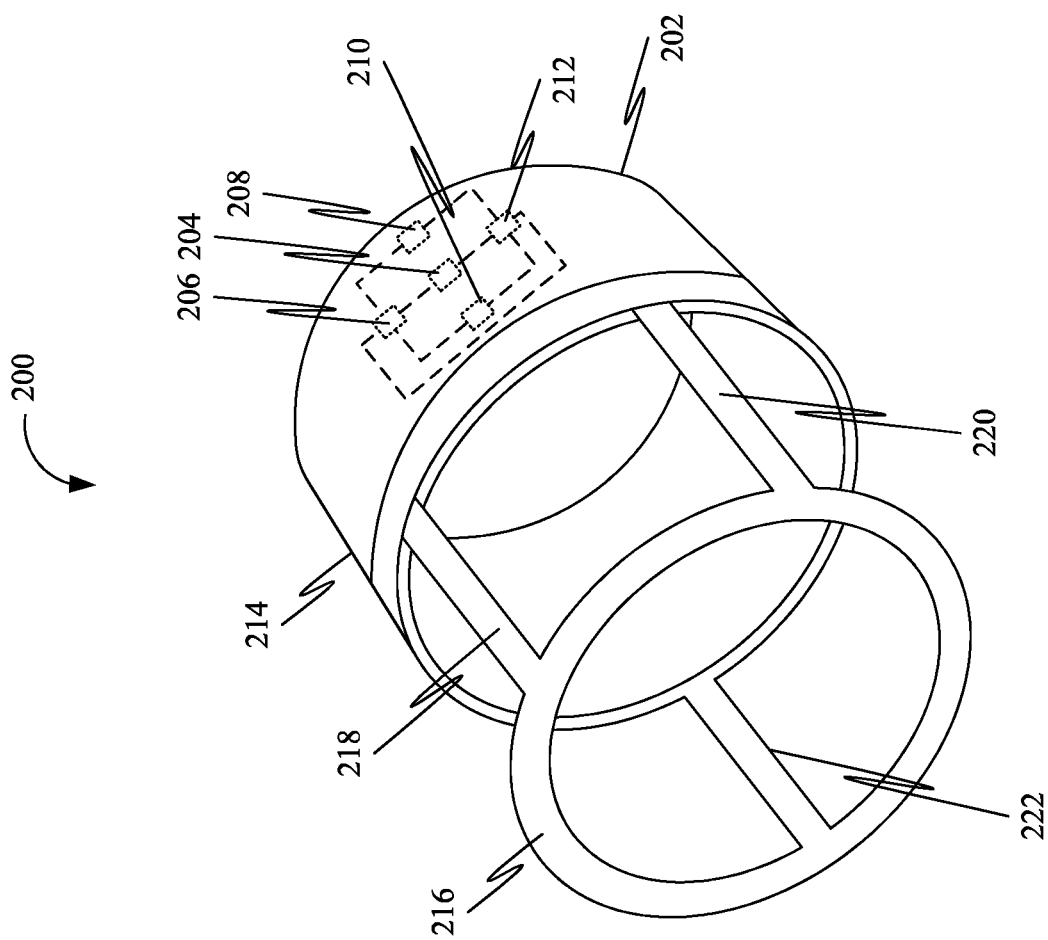
FIG. 2 is a perspective view of a smart lid sleeve system, in accordance with some embodiments.

FIG. 2 is a perspective view of a smart lid sleeve system 200, in accordance with some embodiments. Accordingly, the smart lid sleeve system 200 may include a lid sleeve 202, at least one sensor 204, a processing device 206, a storage device 208, a transmitter 210, and a power source 212.

Further, the lid sleeve 202 may include a first part 214 and a second part 216. Further, the first part 214 may be configured to attach to a lid of a container. Further, the second part 216 may be configured to attach to a neck of the container proximal to a container opening of the container. Further, the lid may be configured to be openably coupled with the container opening. Further, the lid may be associated with a plurality of coupling states in relation to the container opening.

Further, the at least one sensor 204 disposed on the lid sleeve 202. Further, the at least one sensor 204 may be configured for generating at least one sensor data. Further, the at least one sensor data corresponds to the plurality of coupling states.

Further, the processing device 206 may be communicatively coupled with the at least one sensor 204. Further, the processing device 206 may be further configured for analyzing the at least one sensor data. Further, the processing device 206 is further configured for generating at least one notification based on the analyzing. Further, the at least one notification may include a coupling indicator associated with the lid. Further, the coupling indicator may be associated with the plurality of coupling states of the lid. Further, the at least one notification may include alerts and reminders for a scheduled task associated with the container. Further, the at least one notification may include a notification of pilferage, compliance, and alert of any unwanted activity associated with the container.

Further, the storage device 208 configured for storing the at least one notification.

Further, the transmitter 210 may be communicatively coupled with the processing device 206. Further, the transmitter 210 may be configured for transmitting the at least one notification to at least one user device associated with at least one user. Further, the at least one user may be associated with the lid sleeve 202. Further, the at least one user may include an individual, an institution, an organization, etc. that may want to receive the at least one notification. Further, the at least one user device may include a computing device such as, but not limited to, a smartphone, a smartwatch, a tablet, a personal computer (PC), a desktop, a laptop, and so on.

Further, the power source 212 may be electrically coupled with the at least one sensor 204, the transmitter 210, the processing device 206, and the storage device 208. Further, the power source 212 may be disposed on the lid sleeve 202.

Further, in some embodiments, the at least one notification may be transmitted to the at least one user device over at least one of a wired communication channel and a wireless communication channel.

Further, in some embodiments, the at least one sensor 204 may include an identification sensor. Further, the at least one sensor data may include identification data. Further, the identification data corresponds to an indication of the at least one user. Further, the at least one notification may include a user identification associated with the at least one user.

Further, in some embodiments, the plurality of coupling states may include at least one closed state and an open state. Further, at least one object stored in the container may be inaccessible in the at least one closed state. Further, the at least one object stored in the container may be accessible in the open state.

Further, in some embodiments, the storage device 208 may be further configured for retrieving schedule data associated with at least one object stored in the container from a database. Further, the processing device 206 may be further configured for analyzing the schedule data and the at least one sensor data. Further, the at least one notification may include a reminder associated with the at least one object.

In further embodiments, an output device associated with the lid sleeve 202. Further, the output device may be communicatively coupled with the processing device 206. Further, the output device may be further configured to display the at least one notification.

Further, in some embodiments, the lid sleeve 202 may be associated with a unique identity. Further, the storage device 208 may be configured for storing the at least one notification and the unique identity.

Further, in some embodiments, the first part 214 of the lid sleeve 202 may include a top surface and a bottom surface. Further, the transmitter 210 may be disposed on the top surface.

Figure 3:
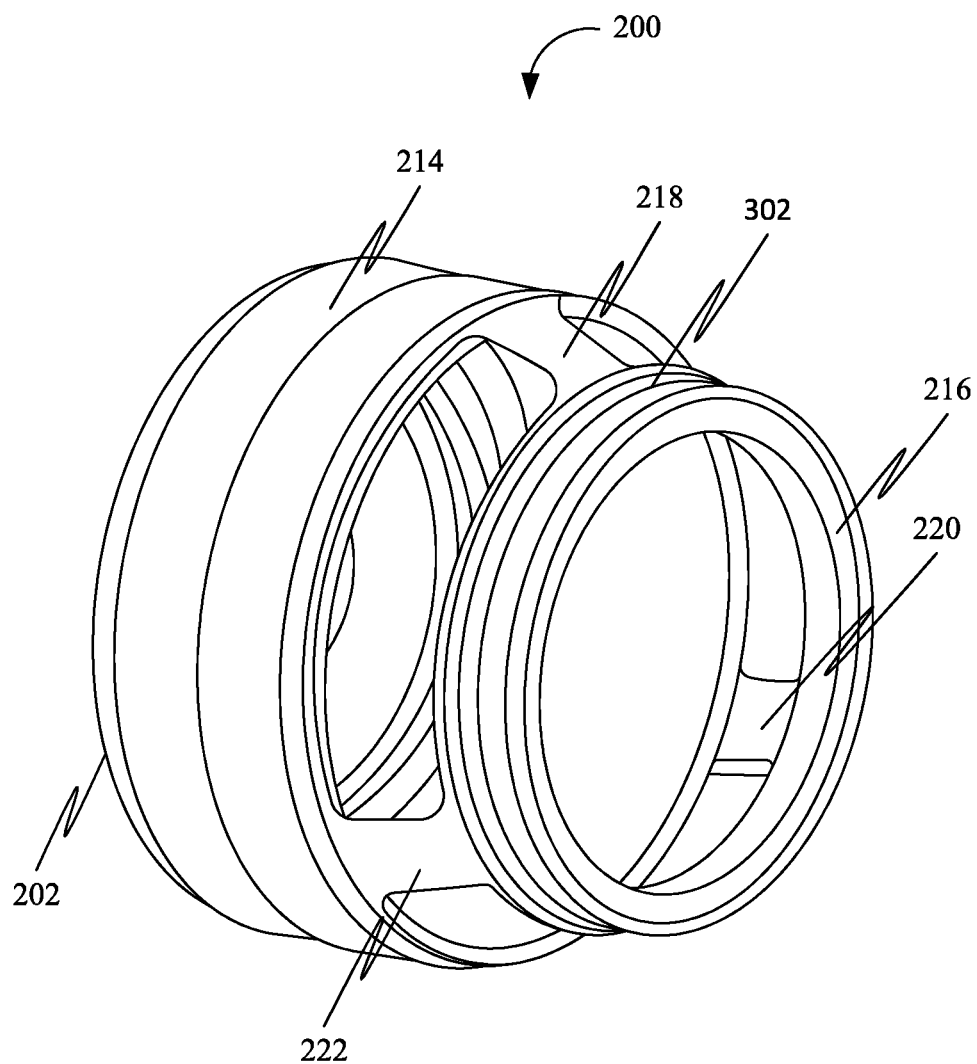
FIG. 3 is a perspective view of the smart lid sleeve system, in accordance with some embodiments.

Further, in some embodiments, the at least one sensor 204 may be disposed on the first part 214. Further, a magnetic strip 302 as shown in FIG. 3 may be disposed on the second part 216. Further, the magnetic strip 302 may be configured for producing the magnetic field. Further, each coupling state of the plurality of coupling states may be associated with a strength of the magnetic field. Further, in an embodiment, the at least one sensor 204 may include at least one of a magneto-resistive sensor and a hall effect sensor. Further, the at least one sensor 204 may be configured for generating the at least one sensor data based on the strength of the magnetic field.

Further, in some embodiments, the first part 214 may be attached to the second part 216 using at least one coupler 218-222. Further, the at least one coupler 218-222 may include a resilient material facilitating the lid to transition between the plurality of coupling states.

Further, in some embodiments, the first part 214 may be detachably attached to the second part 216 using at least one coupler 218-222. Further, the at least one coupler 218-222 may be configured to be removed facilitating the lid to transition between the plurality of coupling states.

FIG. 3 is a perspective view of the smart lid sleeve system 200, in accordance with some embodiments.

Figure 4:
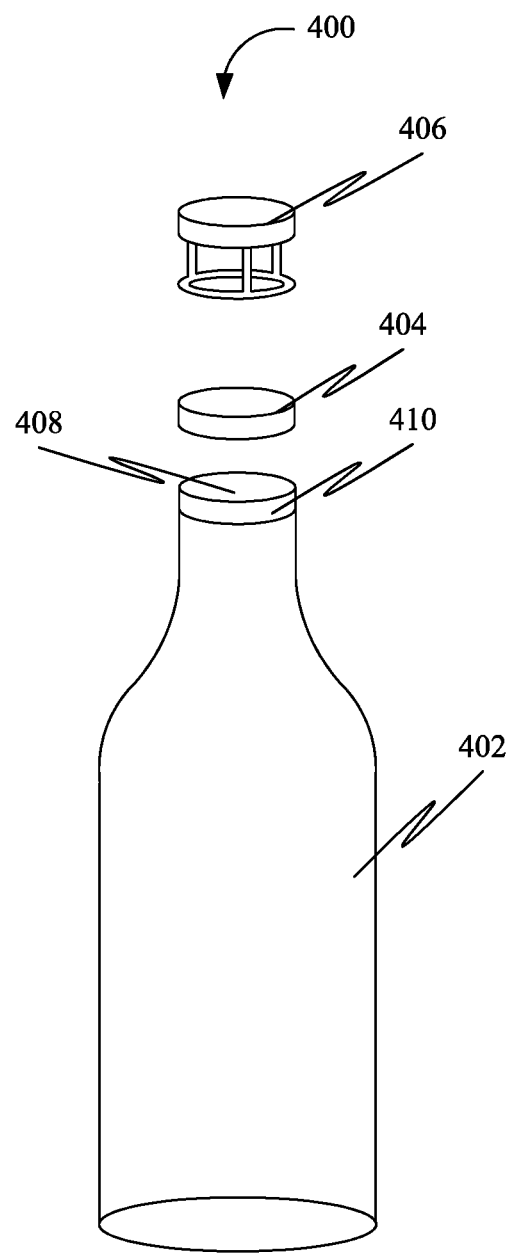
FIG. 4 is an exploded view of a smart lid sleeve system, in accordance with some embodiments.

FIG. 4 is an exploded view of a smart lid sleeve system 400, in accordance with some embodiments. Accordingly, the smart lid sleeve system 400 may include a container 402, a lid 404, a lid sleeve 406, at least one sensor 504, a processing device 506, a storage device 508, a transmitter 510, and a power source 512 as shown in FIG. 5.

Further, the container 402 may be configured to store at least one object (not shown). Further, the container 402 may include a container opening 408 and a container neck 410. Further, the container opening 408 may be shaped in at least one opening shape.

Further, the lid 404 may be configured to be openably coupled with the container opening 408. Further, the lid 404 may be associated with a plurality of coupling states in relation to the container opening 408.

Figure 5:
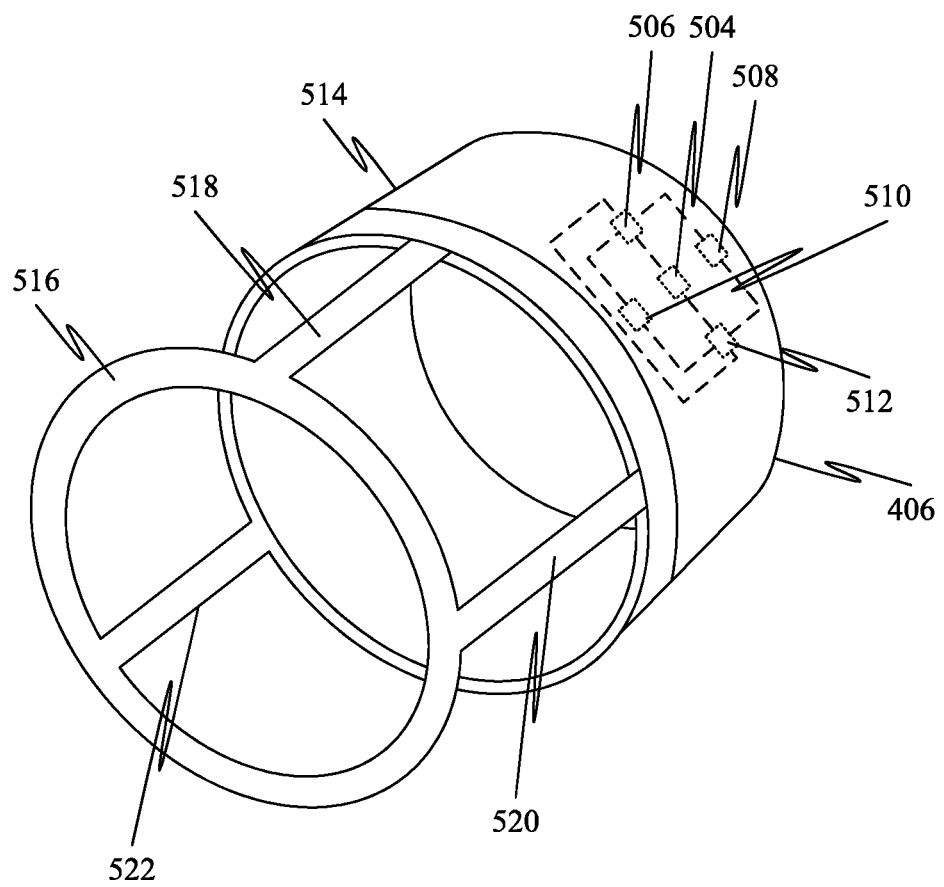
FIG. 5 is an enlarged view of a lid sleeve of the smart lid sleeve system, in accordance with some embodiments.

Further, the lid sleeve 406 may include a first part 514 and a second part 516, as shown in FIG. 5. Further, the first part 514 may be configured to attach to the lid 404. Further, the second part 516 may be configured to attach to the neck 410 of the container 402 proximal to the container opening 408.

Further, the at least one sensor 504 disposed on the lid sleeve 406. Further, the at least one sensor 504 may be configured for generating at least one sensor data. Further, the at least one sensor data corresponds to the plurality of coupling states.

Further, the processing device 506 communicatively coupled with the at least one sensor 504. Further, the processing device 506 may be further configured for analyzing the at least one sensor data. Further, the processing device 506 may be further configured for generating at least one notification based on the analyzing. Further, the at least one notification may include a coupling indicator associated with the lid 404.

Further, the storage device 508 may be configured for storing the at least one notification.

Further, the transmitter 510 may be communicatively coupled with the processing device 506. Further, the transmitter 510 may be configured for transmitting the at least one notification to at least one user device associated with at least one user. Further, the at least one user may be associated with the lid sleeve 406. Further, the at least one user may include an individual, an institution, an organization, etc. that may want to receive the at least one notification. Further, the at least one user device may include a computing device such as, but not limited to, a smartphone, a smartwatch, a tablet, a personal computer (PC), a desktop, a laptop, and so on.

Further, the power source 512 may be electrically coupled with the at least one sensor 504, the transmitter 510, the processing device 506, and the storage device 508. Further, the power source 512 may be disposed on the lid sleeve 406.

Further, in some embodiments, the at least one sensor 504 may include an identification sensor. Further, the at least one sensor data may include identification data. Further, the identification data corresponds to an indication of the at least one user. Further, the at least one notification may include a user identification associated with the at least one user.

Further, in some embodiments, the plurality of coupling states may include at least one closed state and an open state. Further, the at least one object stored in the container may be inaccessible in the at least one closed state. Further, the at least one object stored in the container may be accessible in the open state.

Further, in some embodiments, the storage device 508 may be further configured for retrieving schedule data associated with the at least one object stored in the container from a database. Further, the processing device 506 may be further configured for analyzing the schedule data and the at least one sensor data. Further, the at least one notification may include a reminder associated with the at least one object.

In further embodiments, an output device may be associated with the lid sleeve 406. Further, the output device may be communicatively coupled with the processing device 506. Further, the output device may be further configured to display the at least one notification.

Further, in some embodiments, the lid sleeve 406 may be associated with a unique identity. Further, the storage device 508 may be configured for storing the at least one notification and the unique identity.

Further, in some embodiments, the first part 514 may be attached to the second part 516 using at least one coupler 518-522. Further, the at least one coupler 518-522 may include a resilient material facilitating the lid 404 to transition between the plurality of coupling states.

Further, in some embodiments, the first part 514 may be detachably attached to the second part 516 using at least one coupler 518-522. Further, the at least one coupler 518-522 may be configured to be removed facilitating the lid 404 to transition between the plurality of coupling states.

FIG. 5 is an enlarged view of a lid sleeve 406 of the smart lid sleeve system 500, in accordance with some embodiments.

Figure 6:
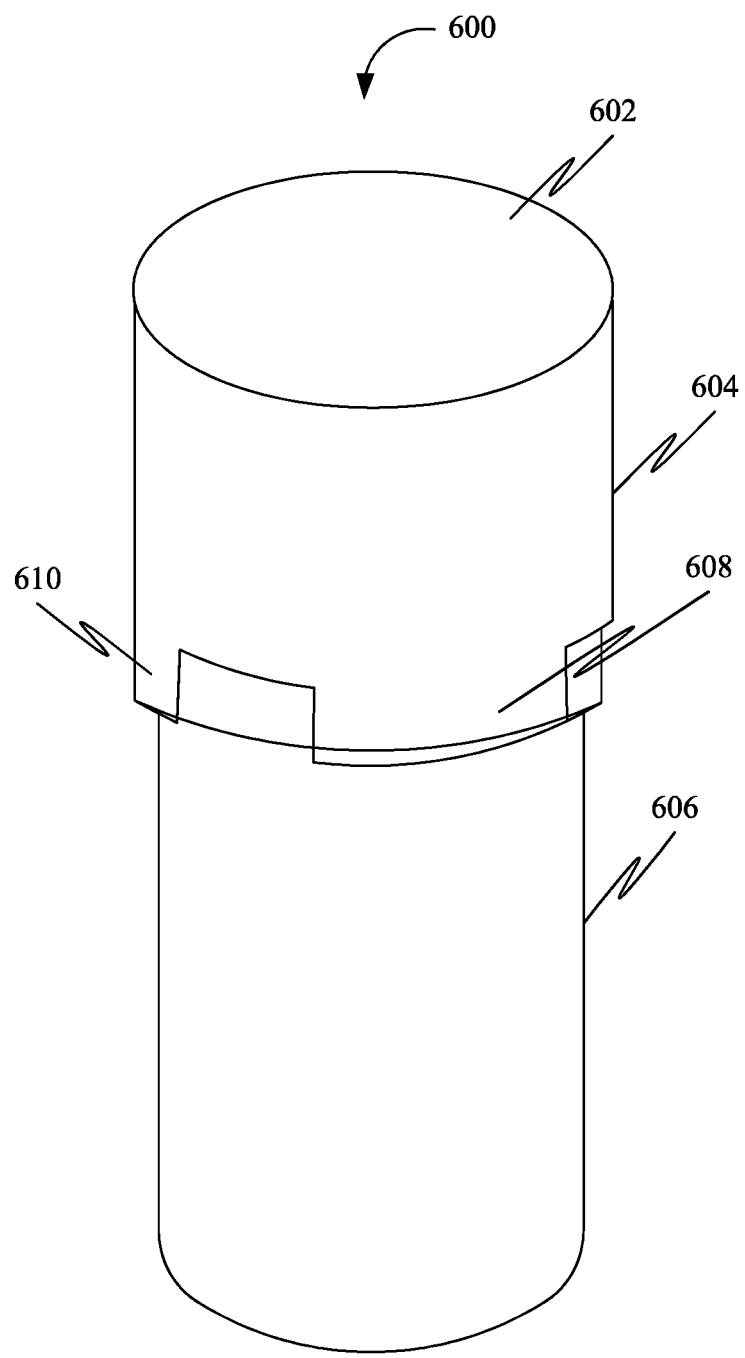
FIG. 6 is a perspective view of a smart lid sleeve system, in accordance with some embodiments.
Figure 7:
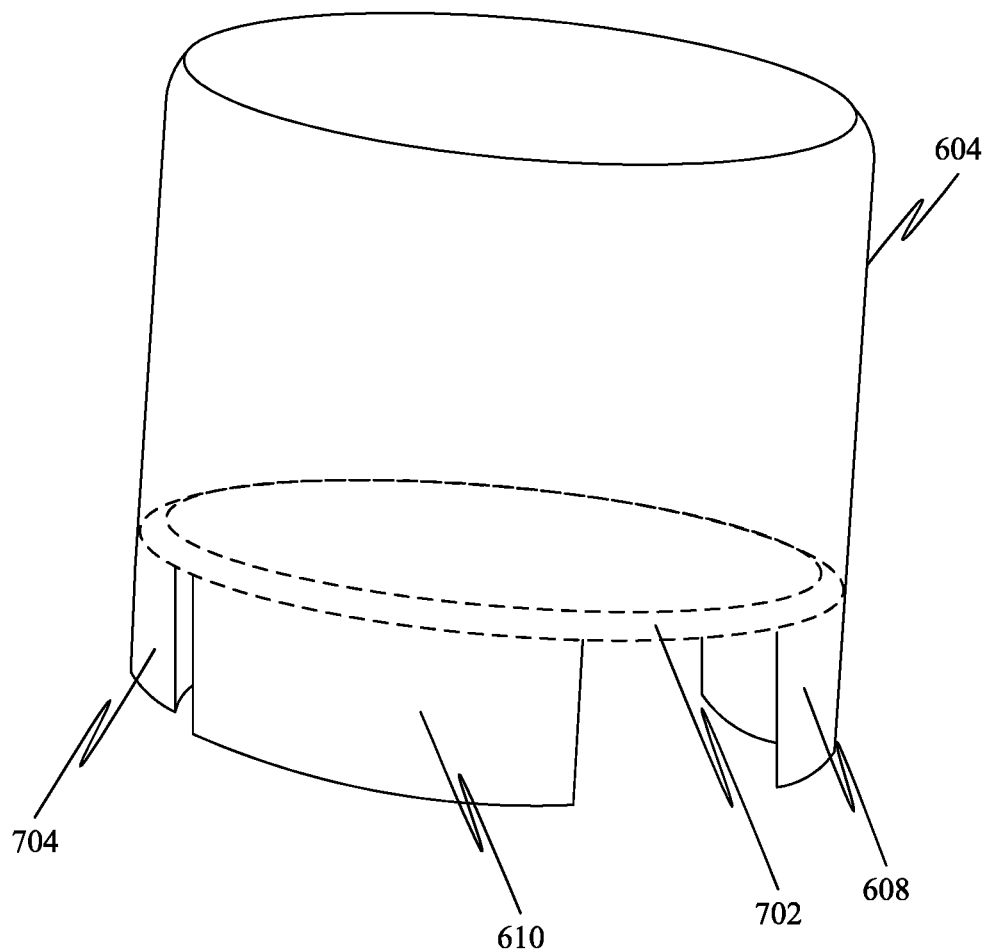
FIG. 7 is a perspective view of a first part of a lid sleeve of the smart lid sleeve system, in accordance with some embodiments.

FIG. 6 is a perspective view of a smart lid sleeve system 600, in accordance with some embodiments. Accordingly, the smart lid sleeve system 600 may include a lid sleeve 602, a panel 702 as shown in FIG. 7. Further, the lid sleeve 602 may include a first part 604 and a second part 606. Further, the first part 604 may be configured to attach to a lid of a container. Further, the second part 606 may be configured to attach to a neck of the container proximal to a container opening of the container. Further, the lid may be configured to be openably coupled with the container opening.

Further, the panel 702 is configured to disposed of within the first part 604 of the lid sleeve 602. Further, the panel 702 may include at least one sensor (not shown), a processing device (not shown), a storage device (not shown), a transmitter (not shown), and a power source (not shown).

Further, the at least one sensor may be configured for generating at least one sensor data. Further, the at least one sensor data corresponds to the plurality of coupling states.

Further, the processing device may be communicatively coupled with the at least one sensor. Further, the processing device may be further configured for analyzing the at least one sensor data. Further, the processing device is further configured for generating at least one notification based on the analyzing. Further, the at least one notification may include a coupling indicator associated with the lid. Further, the coupling indicator may be associated with the plurality of coupling states of the lid.

Further, the storage device configured for storing the at least one notification.

Further, the transmitter may be communicatively coupled with the processing device. Further, the transmitter may be configured for transmitting the at least one notification to at least one user device associated with at least one user. Further, the at least one user may be associated with the lid sleeve 602. Further, the at least one user may include an individual, an institution, an organization, etc. that may want to receive the at least one notification. Further, the at least one user device may include a computing device such as, but not limited to, a smartphone, a smartwatch, a tablet, a personal computer (PC), a desktop, a laptop, and so on.

Further, the power source may be electrically coupled with the at least one sensor, the transmitter, the processing device, and the storage device.

Further, the first part 604 may be attached to the second part 606 using at least one coupler (608, 610 and 704 as shown in FIG. 7). Further, the at least one coupler (608, 610 and 704) may include a resilient material facilitating the lid to transition between the plurality of coupling states. Further, the first part 604 may be detachably attached to the second part 606 using at least one coupler (608, 610 and 704). Further, the at least one coupler (608, 610 and 704) may be configured to be removed facilitating the lid to transition between the plurality of coupling states.

FIG. 7 is a perspective view of a first part 604 of a lid sleeve 602 of the smart lid sleeve system 600, in accordance with some embodiments.

Figure 8:
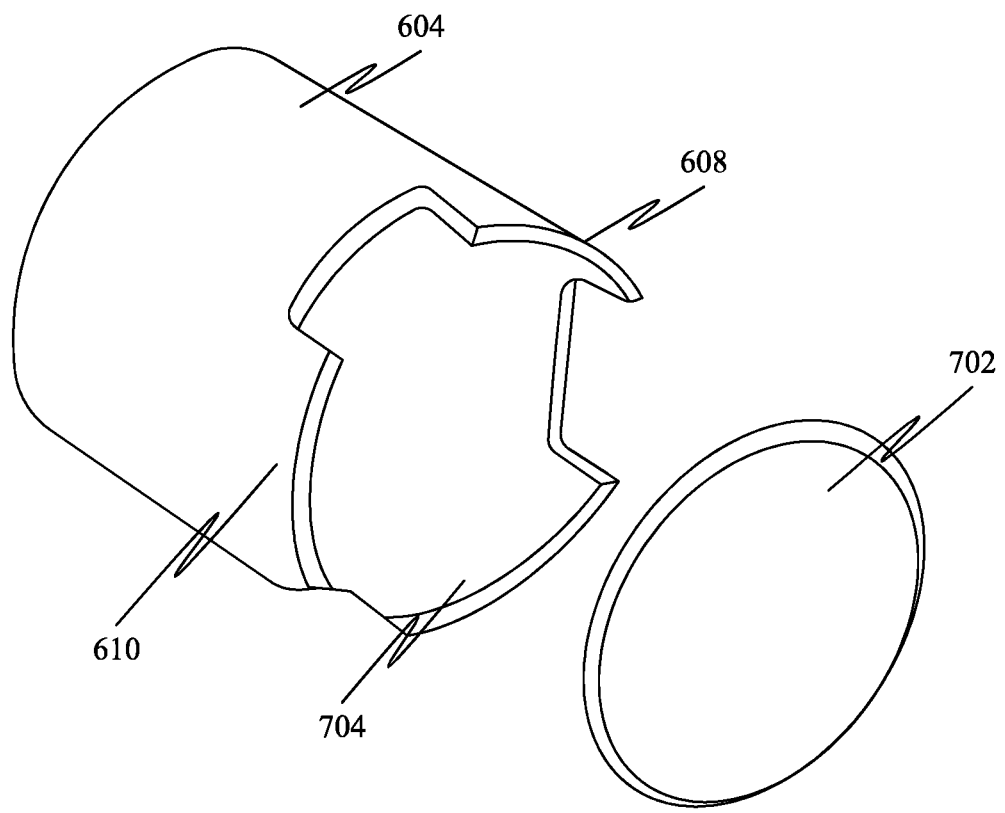
FIG. 8 is an exploded view of the first part of the lid sleeve of the smart lid sleeve system 600, in accordance with some embodiments.

FIG. 8 is an exploded view of the first part 604 of the lid sleeve 602 of the smart lid sleeve system 600, in accordance with some embodiments.

Figure 9:
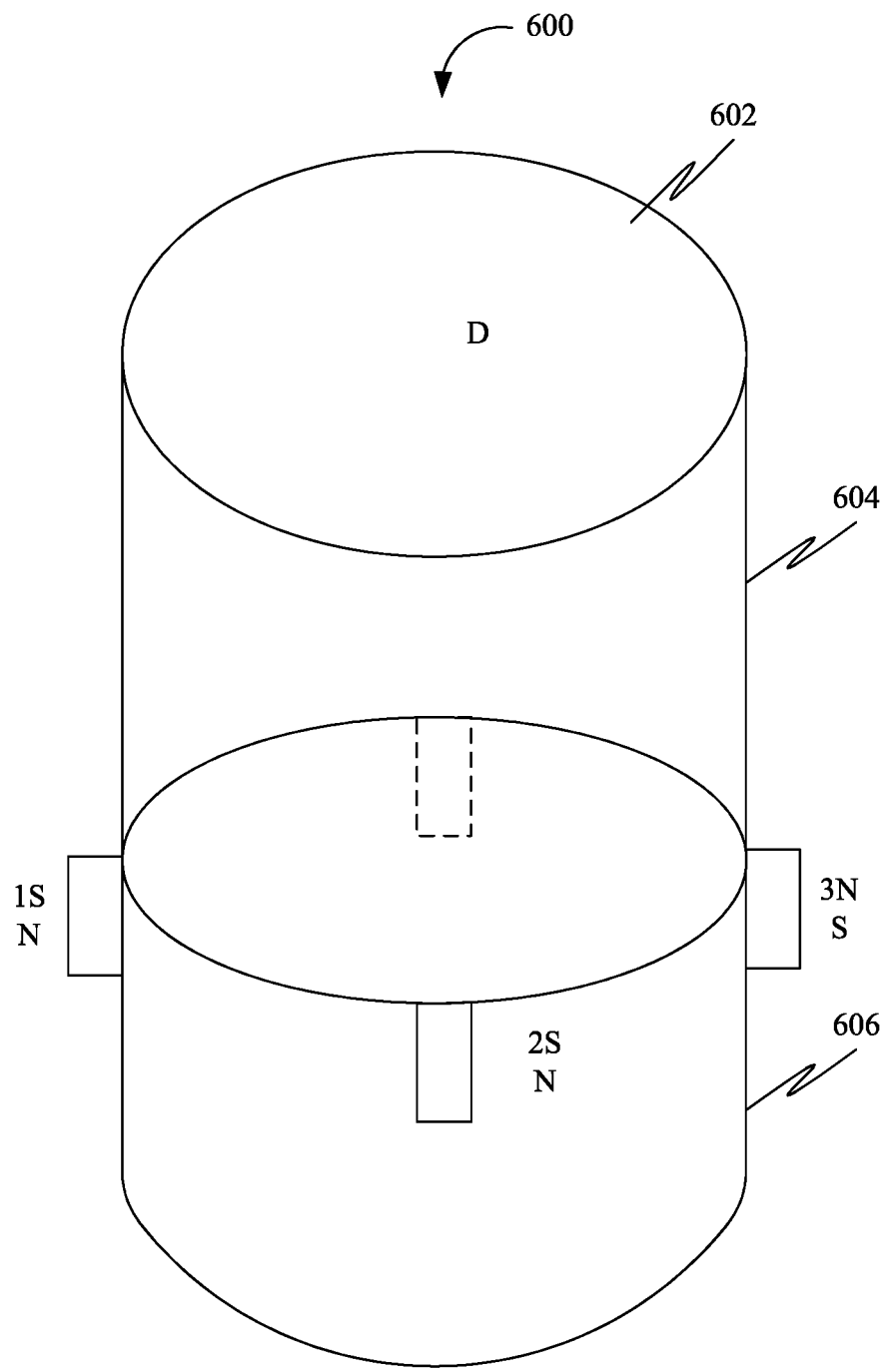
FIG. 9 is a perspective view of the smart lid sleeve system, in accordance with some embodiments.

FIG. 9 is a perspective view of the smart lid sleeve system 600, in accordance with some embodiments.

Figure 10:
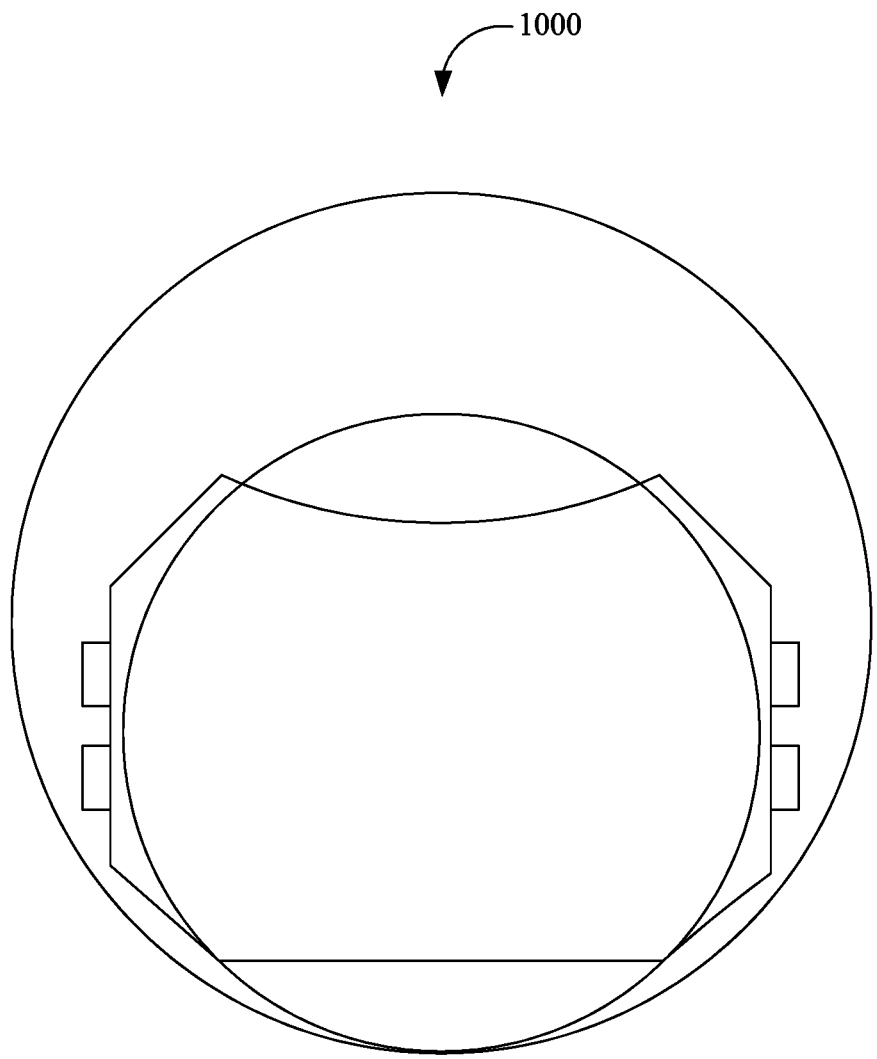
FIG. 10 is a schematic of an assembly top of a smart lid system, in accordance with some embodiments.
Figure 11:
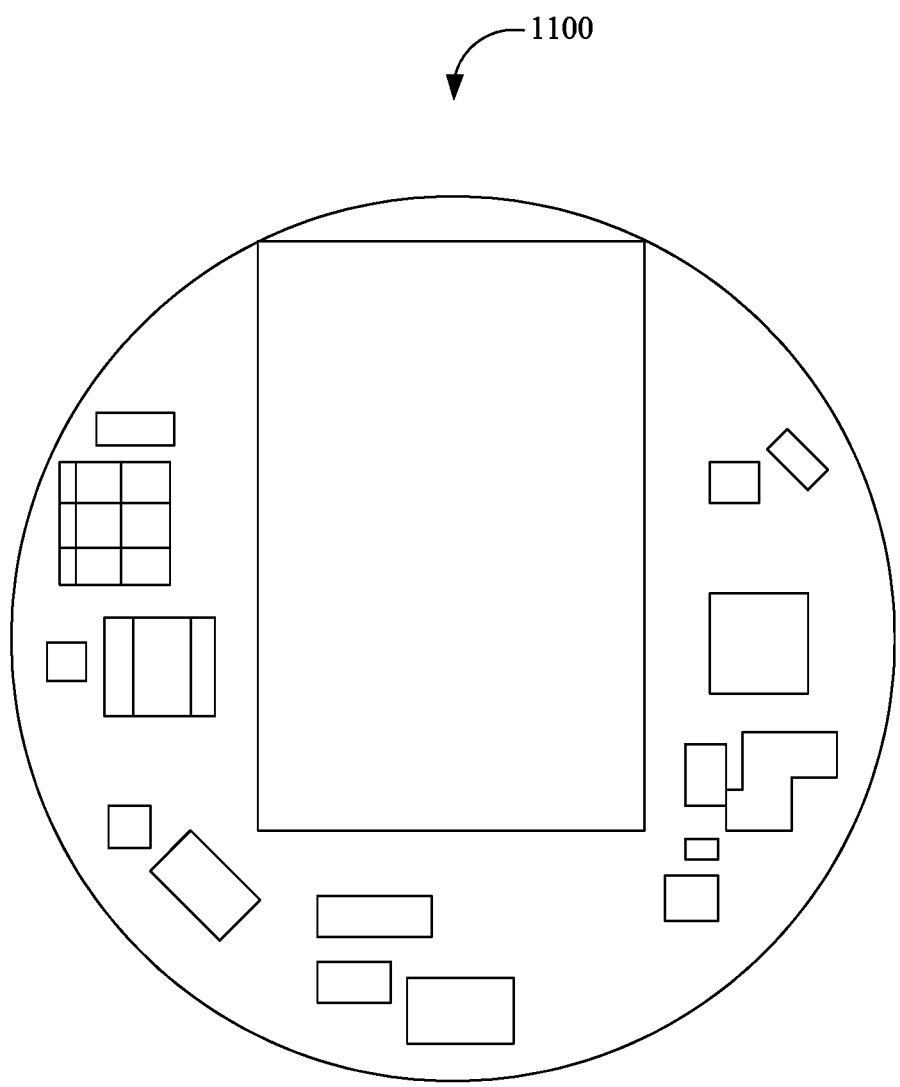
FIG. 11 is a schematic of an assembly bottom of a smart lid system, in accordance with some embodiments.
Figure 12:
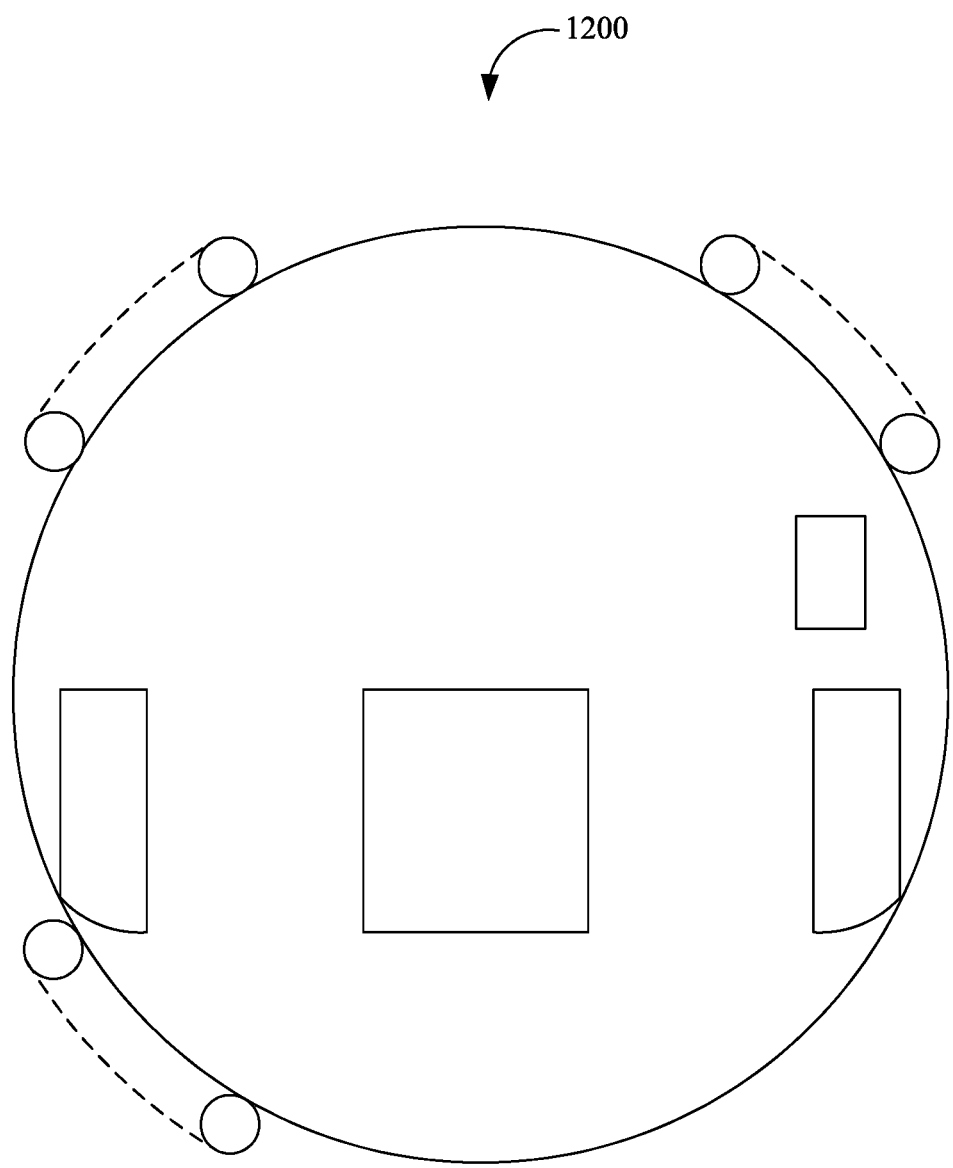
FIG. 12 is a schematic of a top solder of a smart lid system, in accordance with some embodiments.
Figure 13:
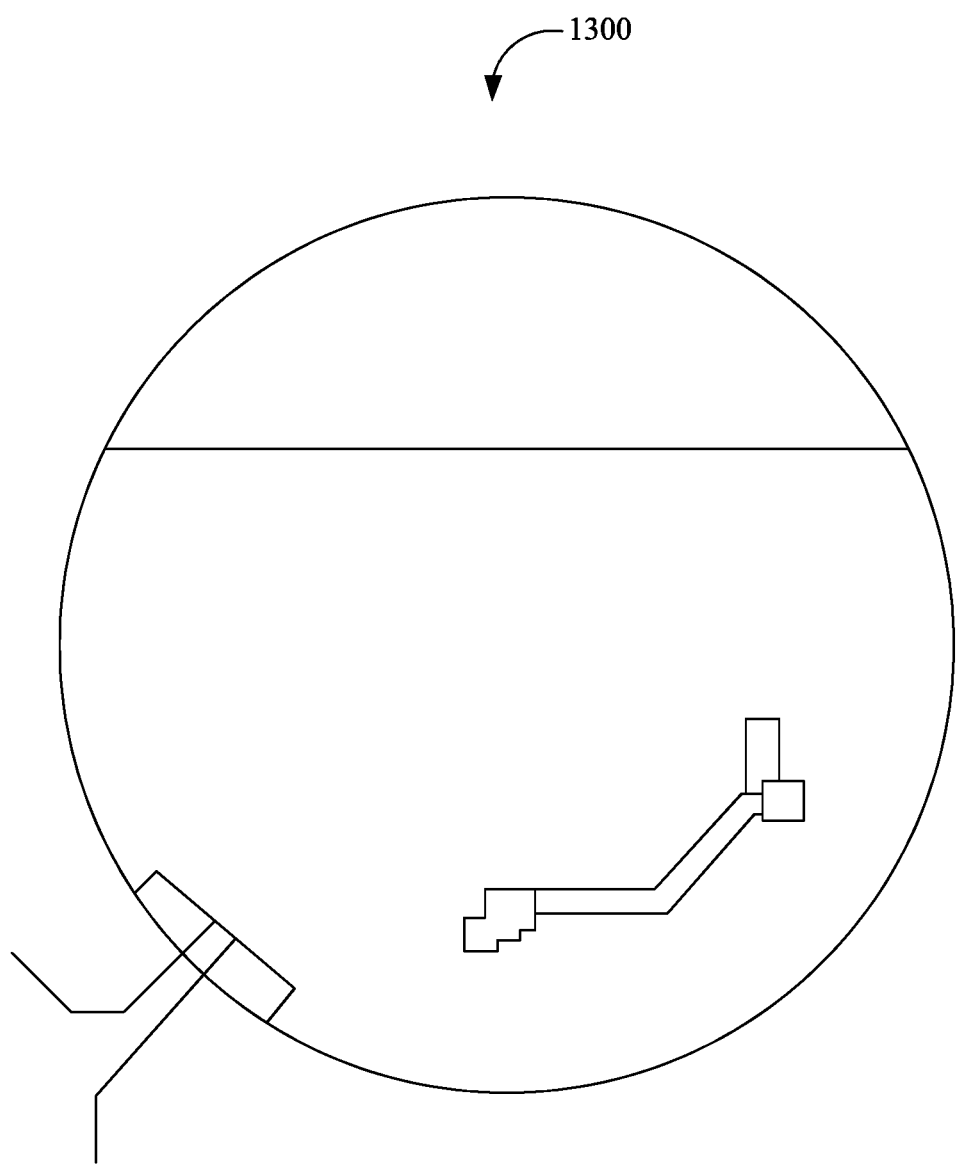
FIG. 13 is a schematic of a top layer of a smart lid system, in accordance with some embodiments.
Figure 14:
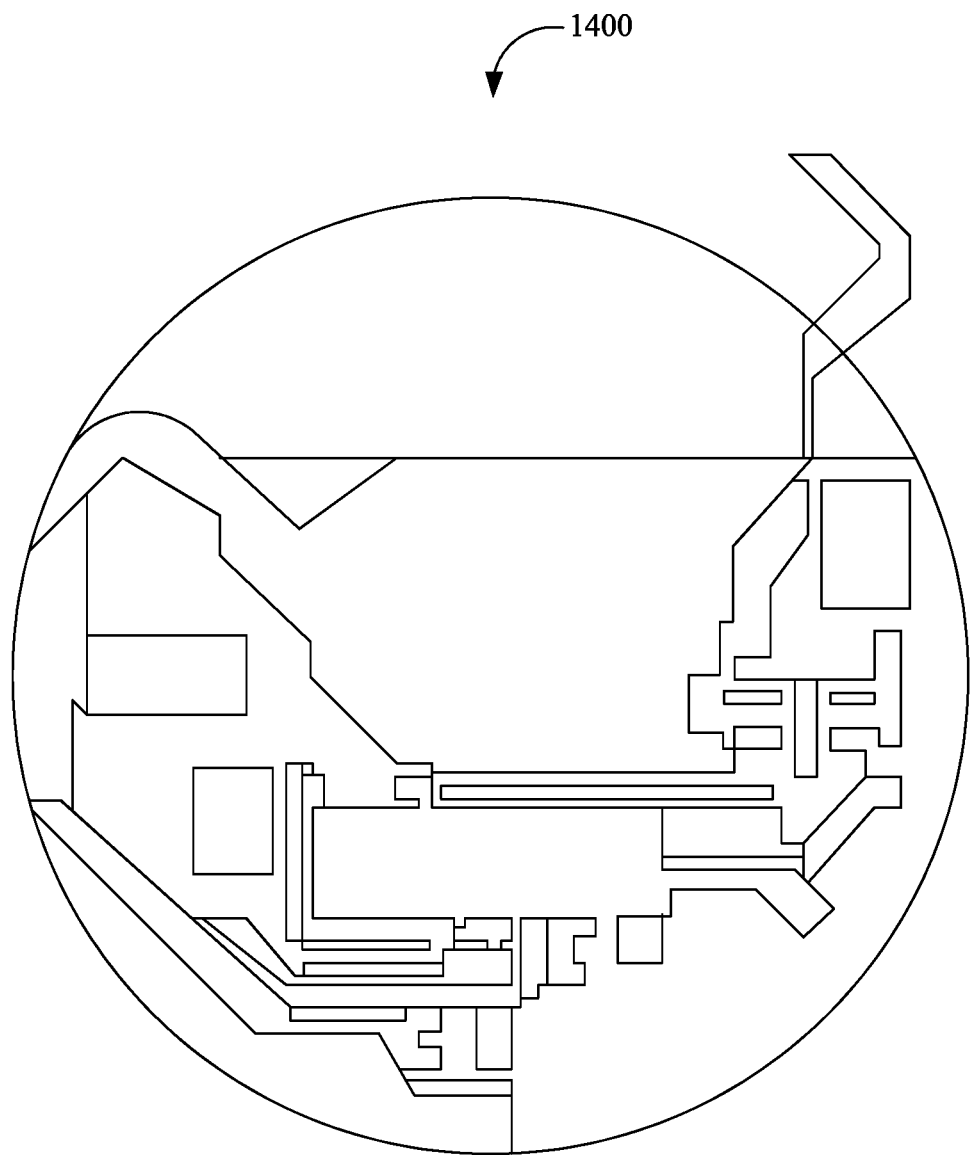
FIG. 14 is a schematic of a bottom layer of a smart lid system, in accordance with some embodiments.
Figure 15:
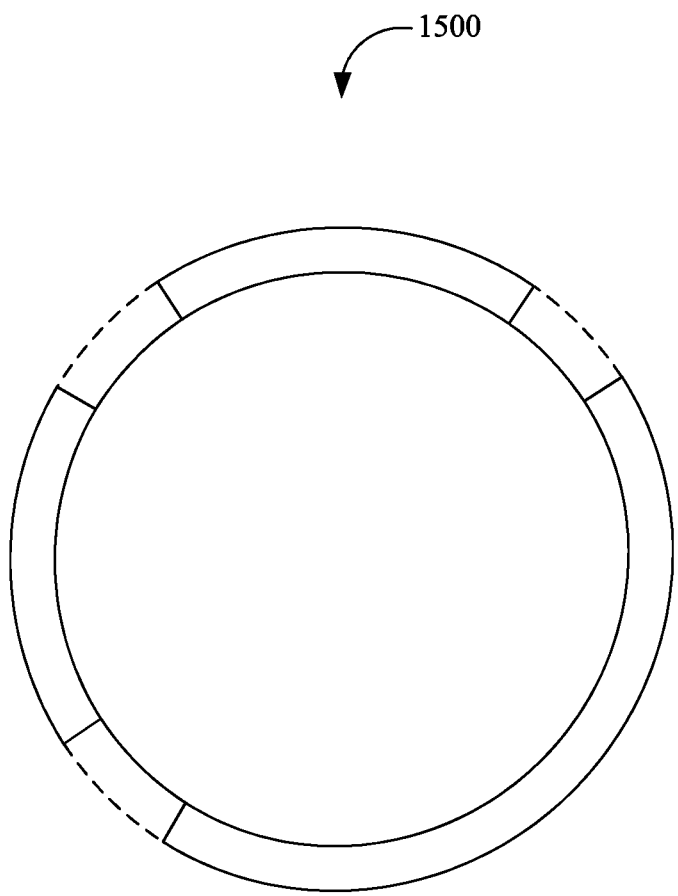
FIG. 15 is a schematic of a magnet of a smart lid system, in accordance with some embodiments.

According to some embodiments, the disclosed smart lid sleeve system may include one or more components such as an assembly top 1000 (shown in FIG. 10), an assembly bottom 1100 (shown in FIG. 11), a top solder 1200 (shown in FIG. 12), a top layer 1300 (shown in FIG. 13), a bottom layer 1400 (shown in FIG. 14) and a magnet 1500 (shown in FIG. 15).

Figure 16:
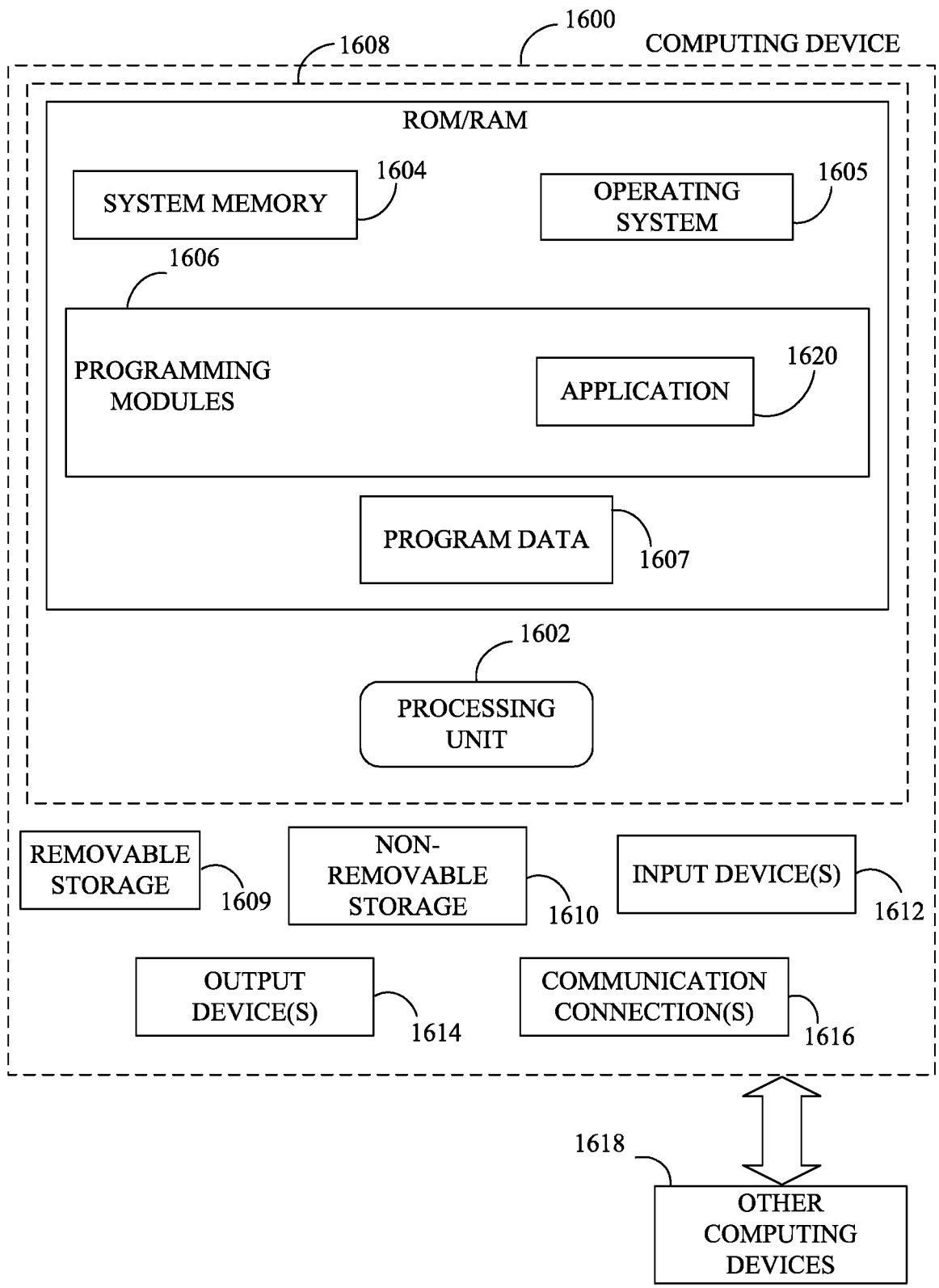
FIG. 16 is a block diagram of a computing device for implementing the methods disclosed herein, in accordance with some embodiments.

With reference to FIG. 16, a system consistent with an embodiment of the disclosure may include a computing device or cloud service, such as computing device 1600. In a basic configuration, computing device 1600 may include at least one processing unit 1602 and a system memory 1604. Depending on the configuration and type of computing device, system memory 1604 may comprise, but is not limited to, volatile (e.g. random-access memory (RAM)), non-volatile (e.g. read-only memory (ROM)), flash memory, or any combination. System memory 1604 may include operating system 1605, one or more programming modules 1606, and may include a program data 1607. Operating system 1605, for example, may be suitable for controlling computing device 1600's operation. In one embodiment, programming modules 1606 may include the image-processing module, machine learning module. Furthermore, embodiments of the disclosure may be practiced in conjunction with a graphics library, other operating systems, or any other application program and is not limited to any particular application or system. This basic configuration is illustrated in FIG. 16 by those components within a dashed line 1608.

Computing device 1600 may have additional features or functionality. For example, computing device 1600 may also include additional data storage devices (removable and/or non-removable) such as, for example, magnetic disks, optical disks, or tape. Such additional storage is illustrated in FIG. 16 by a removable storage 1609 and a non-removable storage 1610. Computer storage media may include volatile and non-volatile, removable and non-removable media implemented in any method or technology for storage of information, such as computer-readable instructions, data structures, program modules, or other data. System memory 1604, removable storage 1609, and non-removable storage 1610 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1600. Any such computer storage media may be part of device 1600. Computing device 1600 may also have input device(s) 1612 such as a keyboard, a mouse, a pen, a sound input device, a touch input device, a location sensor, a camera, a biometric sensor, etc. Output device(s) 1614 such as a display, speakers, a printer, etc. may also be included. The aforementioned devices are examples and others may be used.

Computing device 1600 may also contain a communication connection 1616 that may allow device 1600 to communicate with other computing devices 1618, such as over a network in a distributed computing environment, for example, an intranet or the Internet. Communication connection 1616 is one example of communication media. Communication media may typically be embodied by computer-readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer-readable media as used herein may include both storage media and communication media.

As stated above, a number of program modules and data files may be stored in system memory 1604, including operating system 1605. While executing on processing unit 1602, programming modules 1606 (e.g., application 1620 such as a media player) may perform processes including, for example, one or more stages of methods, algorithms, systems, applications, servers, databases as described above. The aforementioned process is an example, and processing unit 1602 may perform other processes.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general-purpose graphics processor-based systems, multiprocessor systems, microprocessor-based or programmable consumer electronics, application-specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer-readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid-state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

What is claimed is:

1. A smart lid sleeve system comprising:
   a lid sleeve comprises a first part and a second part, wherein the first part is configured to attach to a lid of a container, wherein the second part is configured to attach to a neck of the container proximal to a container opening of the container, wherein the lid is configured to be openably coupled with the container opening, wherein the lid is associated with a plurality of coupling states in relation to the container opening;
   at least one sensor disposed on the lid sleeve, wherein the at least one sensor is configured for generating at least one sensor data, wherein the at least one sensor data corresponds to the plurality of coupling states;
   a processing device communicatively coupled with the at least one sensor, wherein the processing device is further configured for:
      analyzing the at least one sensor data; and
      generating at least one notification based on the analyzing, wherein the at least one notification comprises a coupling indicator associated with the lid;
   a storage device configured for storing the at least one notification;
   a transmitter communicatively coupled with the processing device, wherein the transmitter is configured for transmitting the at least one notification to at least one user device associated with at least one user;
   a power source electrically coupled with the at least one sensor, the transmitter, the processing device, and the storage device, wherein the power source is disposed on the lid sleeve; and
   wherein the first part is attached to the second part using a plurality of couplers, wherein the plurality of couplers comprise a resilient material facilitating the lid to transition between the plurality of coupling states, wherein one of the plurality of couplers is configured to be cut or torn, wherein remaining of the plurality of couplers is configured to be used as a tether between the first part and the second part.

2. The smart lid sleeve system of claim 1, wherein the at least one notification is transmitted to the at least one user device over at least one of a wired communication channel and a wireless communication channel.

3. The smart lid sleeve system of claim 1, wherein the at least one sensor comprises an identification sensor, wherein the at least one sensor data comprises identification data, wherein the identification data corresponds to an indication of the at least one user, wherein the at least one notification comprises a user identification associated with the at least one user.

4. The smart lid sleeve system of claim 1, wherein the plurality of coupling states comprises at least one closed state and an open state, wherein at least one object stored in the container is inaccessible in the at least one closed state, wherein the at least one object stored in the container is accessible in the open state.

5. The smart lid sleeve system of claim 1, wherein the storage device is further configured for retrieving schedule data associated with at least one object stored in the container from a database, wherein the processing device is further configured for analyzing the schedule data and the at least one sensor data, wherein the at least one notification comprises a reminder associated with the at least one object.

6. The smart lid sleeve system of claim 1 further comprising an output device associated with the lid sleeve, wherein the output device is communicatively coupled with the processing device, wherein the output device is further configured to display the at least one notification.

7. The smart lid sleeve system of claim 1, wherein the lid sleeve is associated with a unique identity, wherein the storage device is configured for storing the at least one notification and the unique identity.

8. The smart lid sleeve system of claim 1, wherein the first part of the lid sleeve comprises a top surface and a bottom surface, wherein the transmitter is disposed on the top surface.

9. The smart lid sleeve system of claim 1, wherein the at least one sensor is disposed on the first part, wherein a magnetic strip is disposed on the second part, wherein the magnetic strip is configured for producing the magnetic field, wherein each coupling state of the plurality of coupling states is associated with a strength of the magnetic field.

10. The smart lid sleeve system of claim 9, wherein the at least one sensor comprises at least one of a magneto-resistive sensor and a hall effect sensor, wherein the at least one sensor is configured for generating the at least one sensor data based on the strength of the magnetic field.

11. The smart lid sleeve system of claim 1, wherein the first part is detachably attached to the second part using the at least one coupler, wherein the at least one coupler is configured to be removed facilitating the lid to transition between the plurality of coupling states.

12. A smart lid sleeve system comprising:
   a container configured to store at least one object, wherein the container comprises a container opening and a container neck, wherein the container opening is shaped in at least one opening shape;
   a lid configured to be openably coupled with the container opening, wherein the lid is associated with a plurality of coupling states in relation to the container opening;
   a lid sleeve comprises a first part and a second part, wherein the first part is configured to attach to the lid, wherein the second part is configured to attach to the neck of the container proximal to the container opening;
   at least one sensor disposed on the lid sleeve, wherein the at least one sensor is configured for generating at least one sensor data, wherein the at least one sensor data corresponds to the plurality of coupling states;
   a processing device communicatively coupled with the at least one sensor, wherein the processing device is further configured for:
      analyzing the at least one sensor data; and
      generating at least one notification based on the analyzing, wherein the at least one notification comprises a coupling indicator associated with the lid;
   a storage device configured for storing the at least one notification;
   a transmitter communicatively coupled with the processing device, wherein the transmitter is configured for transmitting the at least one notification to at least one user device associated with at least one user;
   a power source electrically coupled with the at least one sensor, the transmitter, the processing device, and the storage device, wherein the power source is disposed on the lid sleeve; and
   wherein the first part is attached to the second part using a plurality of couplers, wherein the plurality of couplers comprise a resilient material facilitating the lid to transition between the plurality of coupling states, wherein one of the plurality of couplers is configured to be cut or torn, wherein remaining of the plurality of couplers is configured to be used as a tether between the first part and the second part.

13. The smart lid sleeve system of claim 12, wherein the at least one sensor comprises an identification sensor, wherein the at least one sensor data comprises identification data, wherein the identification data corresponds to an indication of the at least one user, wherein the at least one notification comprises a user identification associated with the at least one user.

14. The smart lid sleeve system of claim 12, wherein the plurality of coupling states comprises at least one closed state and an open state, wherein the at least one object stored in the container is inaccessible in the at least one closed state, wherein the at least one object stored in the container is accessible in the open state.

15. The smart lid sleeve system of claim 12, wherein the storage device is further configured for retrieving schedule data associated with the at least one object stored in the container from a database, wherein the processing device is further configured for analyzing the schedule data and the at least one sensor data, wherein the at least one notification comprises a reminder associated with the at least one object.

16. The smart lid sleeve system of claim 12 further comprising an output device associated with the lid sleeve, wherein the output device is communicatively coupled with the processing device, wherein the output device is further configured to display the at least one notification.

17. The smart lid sleeve system of claim 12, wherein the lid sleeve associated with a unique identity, wherein the storage device is configured for storing the at least one notification and the unique identity.

18. The smart lid sleeve system of claim 12, wherein the first part is detachably attached to the second part using the at least one coupler, wherein the at least one coupler is configured to be removed facilitating the lid to transition between the plurality of coupling states.

* * * * *